(12) United States Patent
Matsumoto et al.

(10) Patent No.: US 9,545,630 B2
(45) Date of Patent: Jan. 17, 2017

(54) METHOD FOR FABRICATING MICROCHIP FOR NUCLEIC ACID AMPLIFICATION REACTION

(71) Applicant: Sony Corporation, Tokyo (JP)

(72) Inventors: Masahiro Matsumoto, Kanagawa (JP); Masaki Sato, Tokyo (JP); Hidetoshi Watanabe, Chiba (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/378,588

(22) PCT Filed: Jan. 16, 2013

(86) PCT No.: PCT/JP2013/050652
§ 371 (c)(1),
(2) Date: Aug. 13, 2014

(87) PCT Pub. No.: WO2013/132891
PCT Pub. Date: Sep. 12, 2013

(65) Prior Publication Data
US 2015/0017318 A1    Jan. 15, 2015

(30) Foreign Application Priority Data

Mar. 8, 2012    (JP) ................................. 2012-052322

(51) Int. Cl.
*C12Q 1/68*    (2006.01)
*B01J 19/00*    (2006.01)
(Continued)

(52) U.S. Cl.
CPC ........ *B01L 3/502707* (2013.01); *B01L 3/5027* (2013.01); *B01L 3/5088* (2013.01); *C12N 15/10* (2013.01); *C12Q 1/6844* (2013.01)

(58) Field of Classification Search
CPC .................... B01J 19/0093; B01L 2300/0654
(Continued)

(56) References Cited

U.S. PATENT DOCUMENTS

| 6,635,295 | B1 | 10/2003 | Horigane |
| 2003/0119042 | A1* | 6/2003 | Manuel ................... C12N 9/96 435/6.14 |

(Continued)

FOREIGN PATENT DOCUMENTS

| CN | 1927394 | 3/2007 |
| CN | 102224260 | 10/2011 |

(Continued)

OTHER PUBLICATIONS

Chinese Office Action issued May 27, 2015, for corresponding Chinese Appln. No. 201380012088.2 (14 pages).
(Continued)

*Primary Examiner* — Cachet Sellman
(74) *Attorney, Agent, or Firm* — K&L Gates LLP

(57) ABSTRACT

Provided is a method for fabricating a microchip for nucleic acid amplification reaction that is capable of simple and highly accurate analysis. Provided is a method for fabricating a microchip for nucleic acid amplification reaction, the method including a solidification step of drying a reagent solution including at least a part of substances required for a nucleic acid amplification reaction, and a containment step of arranging the reagent solution including the solidified substance in wells that serve as a reaction site for a nucleic acid amplification reaction. In the microchip for nucleic acid amplification reaction fabricated by the fabrication method, since substances required for the nucleic acid amplification reaction are contained by being solidified, non-specific amplification is suppressed in a nucleic acid amplification reaction, which enables highly accurate analysis.

7 Claims, 6 Drawing Sheets

(51) Int. Cl.
  *B01L 3/00* (2006.01)
  *C12N 15/10* (2006.01)
(58) Field of Classification Search
  USPC .......................................... 427/2.13; 437/6.1
  See application file for complete search history.

(56) References Cited

U.S. PATENT DOCUMENTS

| 2003/0190608 | A1* | 10/2003 | Blackburn | B01J 19/0093 |
| | | | | 435/6.11 |
| 2008/0070281 | A1* | 3/2008 | White | C12Q 1/686 |
| | | | | 435/91.2 |
| 2010/0196908 | A1* | 8/2010 | Opalsky | B01L 7/52 |
| | | | | 435/6.1 |
| 2011/0171315 | A1 | 7/2011 | Zou et al. | |
| 2011/0262919 | A1* | 10/2011 | Tajima | C12Q 1/6804 |
| | | | | 435/6.11 |
| 2011/0312036 | A1* | 12/2011 | Kojima | C12Q 1/6848 |
| | | | | 435/91.2 |

FOREIGN PATENT DOCUMENTS

| EP | 0726310 | 8/1996 |
| EP | 1374827 | 1/2004 |
| JP | 03-118328 | 5/1991 |
| JP | 08-291078 | 11/1996 |
| JP | 10-234822 | 9/1998 |
| JP | 2010-502199 | 1/2010 |
| JP | 2011-160728 | 8/2011 |
| JP | 2012-080870 | 4/2012 |
| JP | 2012-024072 | 9/2012 |
| WO | 00/70973 | 11/2000 |
| WO | 2011/099251 | 8/2011 |

OTHER PUBLICATIONS

International Search Report issued in connection with International Patent Application No. PCT/JP2013/050652, dated Apr. 2, 2013. (2 pages).
Chinese Office Action issued Nov. 25, 2015 in corresponding Chinese Application No. 201380012088.2.
Japanese Office Action issued Dec. 22, 2015 in corresponding Japanese Application No. 2014-503511.
Extended European Search Report mailed Oct. 1, 2015 in EP Application 13758540.2 (9 pages).
Lutz Riegger. "Back-end Processing in Lab-on-a-Chip Fabrication". Nov. 4, 2010 (Nov. 4, 2010). XP055215239.
Klatser P R et al. "Stabilized, freeze-dried PCR mix for detection of mycobacteria". Journal of Clinical Microbiology. American Society for Microbiology. US. vol. 36. No. 6. Jun. 1, 1998 (Jun. 1, 1998). pp. 1798-1800. XP002592488.

* cited by examiner

METHOD FOR FABRICATING MICROCHIP FOR NUCLEIC ACID AMPLIFICATION REACTION

CROSS REFERENCES TO RELATED APPLICATIONS

The present application is a national stage of International Application No. PCT/JP2013/050652 filed on Jan. 16, 2013 and claims priority to Japanese Patent Application No. 2012-052322 filed on Mar. 8, 2012, the disclosure of which is incorporated herein by reference.

BACKGROUND

The present technology relates to a method for fabricating a microchip for nucleic acid amplification reaction. More specifically, the present technology relates to a microchip for nucleic acid amplification reaction in which a solidified reagent that includes at least one or more kinds of the substances required for a reaction is contained in a well that serves as a reaction site for a nucleic acid amplification reaction.

In recent years, microchips have been developed in which wells and channels for performing chemical and biological analyses are provided on a silicon substrate or a glass substrate by applying micro-machining techniques used in the semiconductor industry. These microchips have begun to be utilized for electrochemical detectors in, for example, liquid chromatography, compact electrochemical sensors in medical service locations and the like.

Analytical systems using such microchips are called µ-TAS (micro-Total-Analysis System), lab-on-a-chip, bio chip or the like. Attention is being paid to such microchips as a technology that enables chemical and biological analyses to be performed faster, with greater efficiency, and a higher level of integration, or that enables the analyzing apparatuses to be reduced in size. µ-TAS, which enables analysis with a small amount of sample and enables the disposable use of microchips, is expected to be applied particularly in biological analyses where precious trace amounts of samples or many specimens are handled.

An applied example of µ-TAS is an optical detection apparatus in which a substance is introduced into a plurality of areas arranged on the microchip, and the substance is optically detected. Such an optical detection apparatus may include a reaction apparatus (for example, a real-time PCR apparatus) that causes a reaction, such as a nucleic acid amplification reaction, between a plurality of substances to proceed in a well on the microchip, and optically detects the produced substances.

Microchip-type nucleic acid amplification apparatuses have conventionally employed a method in which the reaction is performed by mixing in advance all of the reagents and template DNA required for the nucleic acid amplification reaction, and introducing the mixed solution into a plurality of wells arranged on the microchip. However, with this method, since it takes a certain amount of time until the mixed solution is introduced into the wells, there is the problem that during that period the reaction proceeds in the mixed liquid, so that non-specific nucleic acid amplification tends to occur, thereby reducing quantitative performance.

In response to the above problem, for example, JP-A-2011-160728 discloses a microchip in which a plurality of reagents required for a nucleic acid amplification reaction are laminated and fixed in order in the wells.

CITATION LIST

Patent Literature

Patent Literature 1: JP 2011-160728A

SUMMARY

Technical Problem

It is a major object of the present technology to a method for fabricating a microchip for nucleic acid amplification reaction that is capable of simple and highly accurate analysis.

Solution to Problem

According to the first aspect of the present invention in order to achieve the above-mentioned object, there is provided a method for fabricating a microchip for nucleic acid amplification reaction, the method including a solidification step of drying a reagent solution including at least a part of substances required for a nucleic acid amplification reaction, and a containment step of arranging the solidified reagent solution in wells that serve as a reaction site for a nucleic acid amplification reaction.

It is preferred that the solidification step includes a step of freeze-drying the reagent solution.

The method according to the present technology may also include a preparation step of readying, prior to the solidification step, a plurality of the reagent solutions that have different compositions, and the reagent solutions may include a first reagent solution that includes an oligonucleotide primer but not an enzyme, and a second reagent solution that includes an enzyme but not an oligonucleotide primer.

Further, the solidification step may also include a step of individually freeze-drying the first reagent solution and the second reagent solution.

In addition, the containment step may include a step of containing the first reagent solution that has been solidified and that includes two or more kinds of oligonucleotide primer in each of a plurality of the wells.

According to another aspect of the present invention in order to achieve the above-mentioned object, there is provided a method for fabricating a microchip for nucleic acid amplification reaction, the method including, solidifying either one of the first reagent solution and the second reagent solution in the solidification step, and, prior to the containment step, a fixing step of adding the reagent solution not used in the solidification step dropwise into the wells and drying in the wells.

It is preferred that the fixing step includes a step of vacuum-drying the reagent solution.

Advantageous Effects of Invention

According to the present technology, there is provided a microchip for nucleic acid amplification that is capable of simple and highly accurate analysis.

Additional features and advantages are described herein, and will be apparent from the following Detailed Description and the figures.

BRIEF DESCRIPTION OF THE FIGURES

FIG. 2 is a schematic view illustrating a configuration in a well 43 of the microchip 1a.

FIG. 3 is a flowchart illustrating a method for fabricating the microchip 1a.

FIG. 4 is a schematic view illustrating a configuration of a modified embodiment of the microchip 1a.

DETAILED DESCRIPTION

Figure 1:
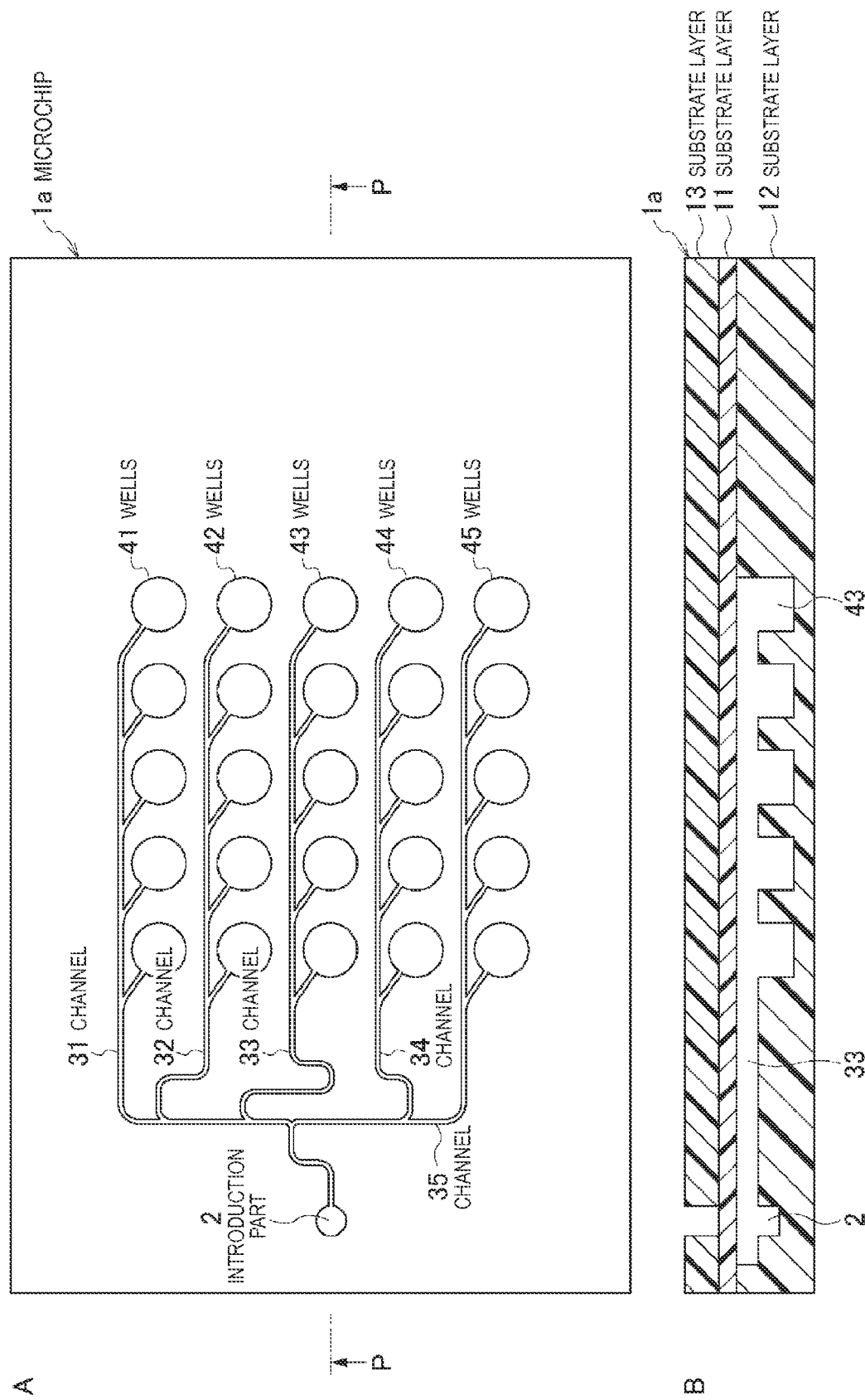
FIG. 1 is a schematic view illustrating a configuration of a microchip 1a according to a first embodiment of the present technology.

Hereinafter, preferred embodiments of the present invention will be described in detail with reference to the appended drawings. Note that, in this specification and the drawings, elements that have substantially the same function and structure are denoted with the same reference signs, and repeated explanation is omitted. The description will be made in the following order.
1. Configuration of the microchip for nucleic acid amplification reaction according to a first embodiment of the present technology
2. Method for fabricating the microchip for nucleic acid amplification reaction according to a first embodiment of the present technology
(1) Molding of the substrate layer
(2) Preparation of the reagent solutions
(3) Solidification of the reagent solutions
(4) Reagent containment
(5) Bonding of the substrate layer
3. Configuration of the microchip for nucleic acid amplification reaction according to a modified embodiment of the first embodiment
4. Configuration of the microchip for nucleic acid amplification reaction according to a second embodiment of the present technology
5. Method for fabricating the microchip for nucleic acid amplification reaction according to a second embodiment of the present technology
(1) Fixing of the reagent solutions
(2) Reagent containment
6. Configuration of the microchip for nucleic acid amplification reaction according to a third embodiment of the present technology

1. Configuration of the Microchip for Nucleic Acid Amplification Reaction According to a First Embodiment of the Present Technology FIG. 1 is a schematic view illustrating a configuration of a microchip 1a according to a first embodiment of the present technology. FIG. 1A is a top face schematic view, and FIG. 1B is a cross-sectional schematic view across the P-P cross-section of FIG. 1A.

The microchip for nucleic acid amplification reaction (hereinafter referred to as "microchip") denoted by reference numeral 1a includes, as an area into which a sample solution is introduced, an introduction part 2 into which a liquid such as a sample is externally introduced, wells 41 to 45 that serve as a reaction site for a nucleic acid amplification reaction, and channels 31 to 35 connecting the introduction part 2 and the respective wells. Further, as described below, reagents R1 and R2 that include at least a part of the substances required in the nucleic acid amplification reaction are contained in the wells 41 to 45 (reagents R1 and R2 are not illustrated in FIG. 1B). In FIG. 1 and the description thereof, the five wells supplied with sample solution by channel 31 are all referred to as wells 41. Similarly, each of the five wells supplied with sample solution by channels 32, 33, 34, and 35 will be collectively described as wells 42, 43, 44, and 45. Further, the term sample solution refers to a solution that includes a nucleic acid such as DNA or RNA, which is a template nucleic acid that is the target of amplification in a nucleic acid amplification reaction.

Examples of the "nucleic acid amplification reaction" performed using the microchip according to the present technology may include a conventional PCR (polymerase chain reaction) that employs thermal cycling, as well as various isothermal amplification methods that do not involve thermal cycling. Examples of isothermal amplification methods include methods such as LAMP (loop-mediated isothermal amplification), SMAP (SMart Amplification Process), NASBA (nucleic acid sequence-based amplification), ICAN® (isothermal and chimeric primer-initiated amplification of nucleic acids), TRC (transcription-reverse transcription concerted), SDA (strand displacement amplification), TMA (transcription-mediated amplification), RCA (rolling circle amplification) and the like. In addition, the "nucleic acid amplification reaction" widely includes nucleic acid amplification reactions that are based on varying temperature or constant temperature, which are directed to the amplification of nucleic acids. Further, such nucleic acid amplification reaction also include reactions that involve quantification of an amplified nucleic acid, such as a real-time PCR method.

The microchip 1a is formed by bonding a substrate layer 11 on a substrate layer 12 on which the introduction part 2, the channels 31 to 35, and the wells 41 to 45 are formed, and then bonding a substrate layer 13 on the substrate layer 11 (refer to FIG. 1B). In the microchip 1a, if the bonding of the substrate layer 11 and the substrate layer 12 is carried out under a pressure lower than atmospheric pressure, the interior of the introduction part 2, the channels 31 to 35, and the wells 41 to 45 can be hermetically sealed at a pressure lower than atmospheric pressure ($1/100$ atmospheric pressure). In the microchip 1a, by making the area into which the sample solution is introduced have a pressure lower than atmospheric pressure, the sample solution is sucked up due to the negative pressure inside the microchip when the sample solution is introduced. Consequently, the introduction of the sample solution into the microchip 1a in which micro channel structures are formed can be carried out in a shorter period of time.

As the material of the substrate layers 11, 12, and 13, glass and various kinds of plastic may be used. Preferably, the substrate layers 12 and 13 are formed from a gas-impermeable material. By using a gas-impermeable material, such as PC, for the substrate layers 12 and 13 that form the outer face of the microchip 1a, the sample solution introduced into the wells 41 to 45 can be prevented from being turned into a gas by the heat of the nucleic acid amplification reaction, and escaping (fluid loss) through the substrate layer 11. Further, when the area of the microchip 1a into which the sample solution is introduced is hermetically sealed due to having a lower pressure than atmospheric pressure, it is also preferred that the substrate layers 12 and 13 is formed from a gas-impermeable material in order to prevent the entry of air from outside of the microchip 1a to maintain the internal negative pressure.

Examples of the material forming the gas-impermeable substrate layers includes glass, plastics, metals, and ceramics. Examples of plastics include PMMA (polymethyl methacrylate acrylic resin), PC (polycarbonate), PS (polystyrene), PP (polypropylene), PE (polyethylene), PET (polyethylene terephthalate), diethylene glycol bis-allyl carbonate, SAN resin (styrene-acrylonitrile copolymer), MS resin (MMA-styrene copolymer), TPX (poly(4-methyl penten-1)), polyolefin, SiMA (siloxanyl methacrylate monomer)-MMA copolymer, SiMA-fluorine containing monomer copolymer, silicon macromer-(A)-HFBuMA (heptafluorobutyl methacrylate)-MMA terpolymer, disubstituted polyacetylene-based polymer and the like. Examples of metals include aluminum, copper, stainless steel (SUS), silicon, titanium, tungsten and the like. Examples of ceramics include alumina ($Al_2O_3$), nitrogen aluminum (AlN), silicon carbide (SiC), titanium oxide ($TiO_2$), zirconia oxide ($ZrO_2$), quartz and the like.

The substrate layer 11 is preferably formed from an elastic material. In the microchip 1a, by forming the substrate layer 11 that seals the introduction part 2 from an elastic material, a portion of a penetrating member, such as a needle, can penetrate the introduction part 2 from outside the microchip 1a. If a syringe connected to the needle is pre-filled with the sample solution, and the substrate layer 11 is penetrated by that needle, the sealed introduction part 2 and the interior of the syringe are connected, and the sample solution can be introduced into the microchip 1a without air bubbles being formed.

Further, when the area into which the sample solution is introduced is hermetically sealed by having a lower pressure than atmospheric pressure, at the point when the tip of the needle reaches the introduction part 2, due to the pressure difference between outside the microchip 1a and the introduction part 2, the sample solution in the syringe is automatically sucked into the introduction part 2.

By forming the substrate layer 11 from an elastic material, when the needle is withdrawn from the introduction part 2 after the sample solution has been introduced, the penetrated location can be naturally sealed due to the self-sealing ability of the substrate layer 11. In an embodiment of the present technology, natural sealing of the penetrated location of the needle due to elastic deformation of the substrate layer is defined as "self-sealing ability".

Examples of the elastic material includes acrylic-based elastomer, urethane-based elastomer, fluorine-based elastomer, styrene-based elastomer, epoxy-based elastomer, and natural rubber, in addition to silicon-based elastomer such as polydimethylsiloxane (PDMS).

Note that, in the case of optically analyzing the substances held in each well of the microchip 1a according to an embodiment of the present technology, it is preferred to select as the material for each of the substrate layers a material that is light transmissive and that has little optical error due to having little intrinsic fluorescence and a small wavelength dispersion.

Figure 2:
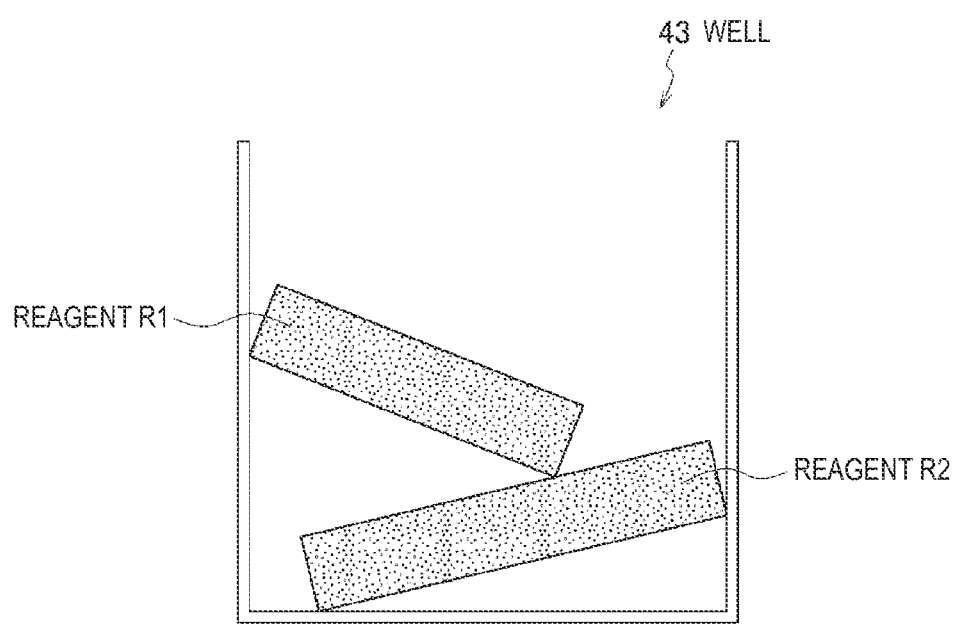

Next, the reagents contained in the wells of the microchip 1a will be described. In FIG. 2A, a well 43 is schematically illustrated as a representative of the wells of the microchip 1a. The well 43 contains solid-phase reagents R1 and R2. The reagents R1 and R2 include at least a part of the substances required to obtain an amplified nucleic acid strand in a nucleic acid amplification reaction. Specific examples include a component included in an oligonucleotide primer (hereinafter sometimes also referred to as "primer"), a nucleic acid monomer (dNTPs), an enzyme, and a reaction buffer solution that is complementary to at least a portion of the base sequence of the DNA, RNA and the like that is the amplification target. In addition, although not directly necessary in a nucleic acid amplification reaction, a probe including a label, such as a fluorescent label, for detecting the amplified nucleic acid strand, a detection reagent that intercalates with double-stranded nucleic acid and the like may also be included in the reagents R1 and R2 as a substance that is used for detection of an amplified nucleic acid strand.

The components required for a nucleic acid amplification reaction that are included in reagent R1 and reagent R2 may be a different composition to each other. For example, reagent R1 may be a reagent solution (a first reagent solution) that includes a primer but does not include an enzyme, and reagent R2 may be a reagent solution (a second reagent solution) that includes an enzyme but does not include a primer. By thus configuring so that an enzyme is not included in reagent R1 that includes a primer, and so that a primer is not included in reagent R2 that includes an enzyme, the primer and the enzyme do not mix until the sample solution is introduced into the wells, which suppresses the occurrence of primer dimers. Alternatively, reagent R1 may be the reagent solution (the second reagent solution) that includes an enzyme but does not include a primer, and reagent R2 may be the reagent solution (the first reagent solution) that includes a primer but does not include an enzyme. The composition of reagents R1 and R2 may be freely selected. It is noted that reagents R1 and R2 are not limited to the shapes illustrated in FIG. 2. They may be any shape as long as they have a volume that can be contained in the well 43. Further, reagents R1 and R2 having the same composition may be contained in the plurality of wells provided in the microchip 1a, or reagents R1 and R2 having different compositions may be contained in each of the wells.

2. Method for Fabricating the Microchip for Nucleic Acid Amplification Reaction According to a First Embodiment of the Present Technology The method for fabricating the microchip 1a will now be described with reference to the flowchart illustrated in FIG. 3.

(1) Molding of the Substrate Layer

Figure 3:
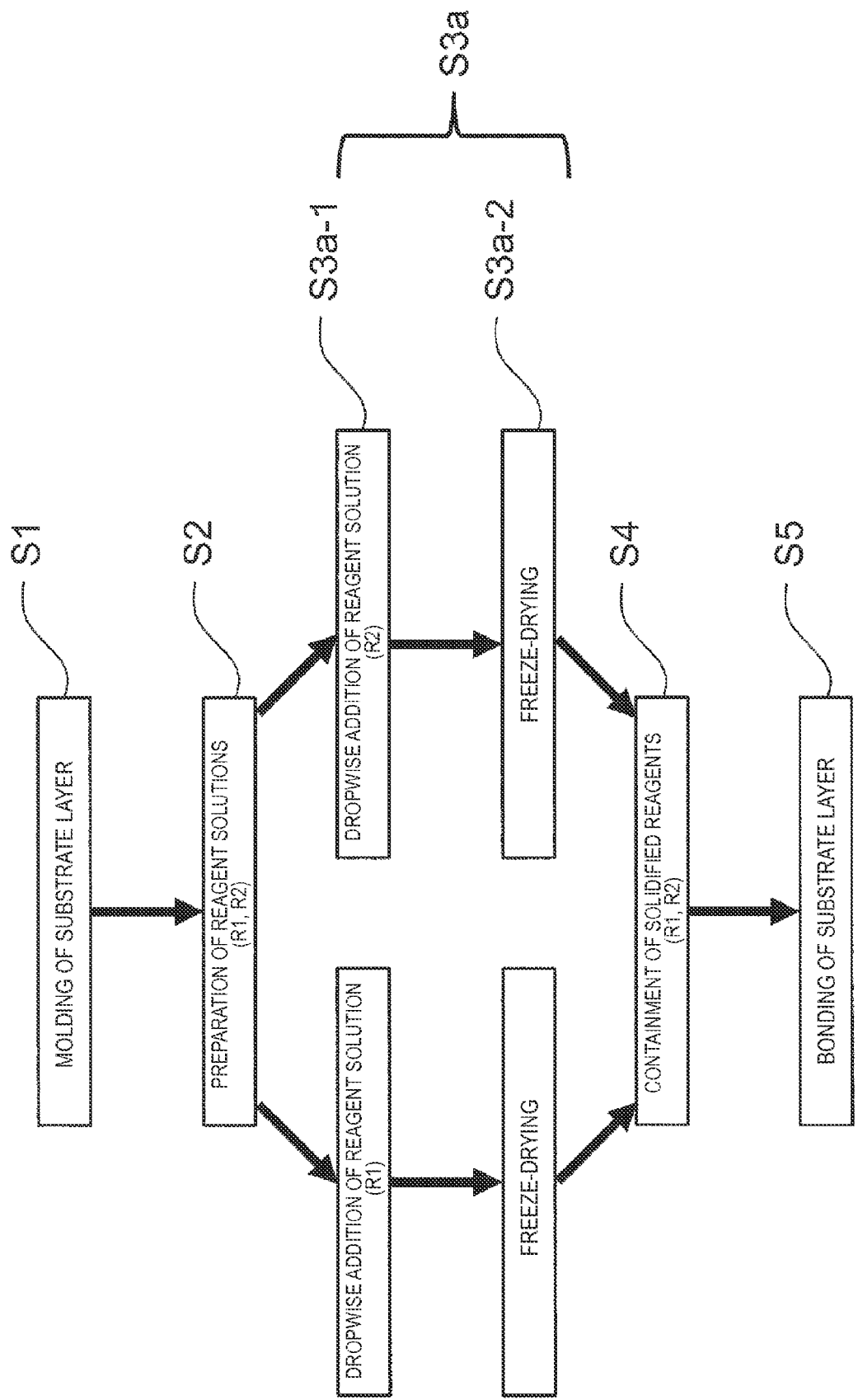

In FIG. 3, reference symbol S1 represents a step of molding the substrate layer. In this step, the introduction part 2, channels 31 to 35, and wells 41 to 45 are formed on the substrate layer 12. The molding of the introduction part 2 and the like onto the substrate layer 12 can be carried out by a known technique. For example, the molding can be carried out by wet etching or dry etching of a glass substrate layer, or by nano-printing, injection molding, or cutting of a plastic substrate layer. Further, the substrate layer 12 and the like can be molded on the substrate layer 11, or some parts may be molded on the substrate layer 11, and the remaining parts molded on the substrate layer 12.

(2) Preparation of the Reagent Solutions

In FIG. 3, reference symbol S2 represents a step of preparing a reagent solution. In this step, a liquid or a gel-like reagent solution is prepared based on the composition of the reagents R1 and R2 to be contained in the microchip 1a. It is sufficient if the reagent solution only includes at least a part of the substances that are required in the nucleic acid amplification reaction, and the composition of the reaction solution may be arbitrarily set. For example, a reagent R1 that includes only a primer and a reagent R2 that only includes an enzyme may be readied. Further, the number of types of reagent solution that are prepared is not limited to two. A single reagent solution may include just one type, or a plurality of types, of the substances required in the nucleic acid amplification reaction.

If a primer is included in the reagent solution readied in the preparation step, one type of primer or a plurality of types of primer may be included. In the method for fabricating the microchip 1a according to the present technology, it is noted that primers including a different base sequence to a primer formed from a given base sequence are counted as a different type of primer. Namely, for a target nucleic acid that is the target of amplification, a primer set pairing a primer designed for a base sequence of one nucleic acid strand with a primer designed for the base sequence of that complementary strand is considered as including two types of primer. The definition of these primer types is the same in the below-described second and third embodiments.

Regarding the composition of the reagent solutions, for example, it is preferred to prepare a reagent solution that includes a primer but does not include an enzyme and a reagent solution that includes an enzyme but does not include a primer, because this means the primer and the enzyme do not mix until the sample solution introduced when the nucleic acid amplification reaction is started reaches the well, which suppresses non-specific amplification of the nucleic acid by primer dimers. Further, it is preferred that the primer-containing reagent solution includes two or more types of primer.

In the reagent solution preparation step S2, it is preferred to hold the reagent solutions, and the primer solution and enzyme solution added to the reaction solutions, at a cool temperature. This holding of the reagent solutions and the like at a cool temperature can be carried out by placing the container containing the reagent solutions and the like on ice, or by placing the equipment holding the tubes of an aluminum block and the like in advance in a freezer, and using in a cooled state.

(3) Solidification of the Reagent Solutions

In FIG. 3, reference symbol S3a represents a step of solidifying the reagent solutions. In this step, the plurality of reagent solutions readied in preparation step S2 are solidified. Namely, in this step the reagent solutions are dried to produce solid-phase reagents R1 and R2. Fixing step S3a will be described by dividing it into two stages, which are, as illustrated in FIG. 3, in order, a "reagent solution dropwise addition" step S3a-1, and a "freeze-drying" step S3a-2. Note that FIG. 3 is a flowchart illustrating a case in which two types of reagent solution were readied in preparation step S2.

Reagent Solution Dropwise Addition Step S3a-1

In this step, a reagent solution prepared in the above-described reagent solution preparation step S2 is added dropwise to a solidification container to be used in solidification step S3a. If a plurality of types of reagent solution were readied in preparation step S2, each of these reagent solutions is individually added dropwise to the solidification container, and individually solidified. Further, even for a case in which reagents R1 with the same composition are to be contained in the plurality of wells 41 to 45 of the microchip 1a, a number of solidification containers that matches the number of wells are readied, and the reagent solutions are added dropwise to the respective solidification container. Although the solidification container may be any material, it is preferred that the solidification container is capable of withstanding the temperature and air pressure set in the subsequent freeze-drying step S3a-2.

Freeze-Drying Step S3a-2

In this step, the above-described reagent solution added dropwise to the container us solidified by drying. As the drying method, for example, freeze-drying is preferred. Further, it is preferred that the freeze-drying includes steps such as pre-freezing, primary drying (sublimation freezing), and secondary drying (removal of bound water). The pre-freezing can be carried out if the freezing temperature is at the eutectic point (temperature at which the reagent solution freezes) or lower. However, in order to prevent enzyme deactivation and completely freeze the reagent solution, it is preferred to freeze at about −40° C. In the primary drying, the reagent solution frozen in the pre-freezing step is dried. At this point, dissolution during the drying process can be prevented and the moisture included in the reagent solution can be sublimed by drying the reagent solution at the eutectic point or lower. The degree of vacuum in the primary drying is desirably 100 Pa or less, for example. The boiling point of water at 100 Pa is about −20° C., which is close to the above-described eutectic point of the reagent solution. Accordingly, dissolution during the drying process is prevented. The degree of vacuum in the primary drying can be appropriately selected based on the eutectic point of the prepared reagent solution. In the secondary drying, water in a molecular state that is adhered to the components included in the reagent solution after the primary drying is removed. The reagent solution can be heated to a temperature at which the components in the reagent solution are not deactivated, denatured or the like, to increase the degree of dryness of the reagent solution. Note that in the method for fabricating a microchip for nucleic acid amplification reaction according to the present technology, the drying method of the solidification step S3a is not limited to freeze-drying.

(4) Reagent Containment

In FIG. 3, reference symbol S4 represents a step of containing the reagents R1 and R2. In this step, the solid-phase reagents R1 and R2 produced in solidification containers in the above-described reagent solution solidification step S3a are removed from the solidification containers, and contained in any one of the wells formed in the substrate layer in the substrate layer molding step S1. The reagents R1 and R2 may be contained in any of the plurality of wells provided on the substrate layer 12, either in one well or in a plurality of wells. Further, the number and type of reagents R1 and R2 contained in one well can be freely set. Reagents R1 and R2 with the same composition or reagents R1 and R2 with different compositions may be contained in a plurality of wells. If a primer is included in reagent R1 or in reagent R2, it is preferred that there is two or more types of primer included in one reagent. For example, a reagent R1 and a reagent R2 each containing different primers may be readied, and the reagents R1 and R2 contained so that they are arranged in separate wells among the plurality of wells provided in the microchip 1a. In such a case, the amplification of a plurality of nucleic acid strands having different base sequences can be analyzed in a single nucleic acid amplification reaction, so that analysis using the microchip 1a is simpler.

(5) Bonding of the Substrate Layer

In FIG. 3, reference symbol S5 represents a substrate layer bonding step. In this step, another substrate layer is bonded on either of the substrate layers in which the reagents R1 and R2 were contained. The bonding of the substrate layers 11, 12, and 13 can be performed by a known method, such as thermal fusion bonding, with an adhesive, anodic bonding, bonding using a pressure-sensitive adhesive sheet, plasma activation bonding, ultrasonic bonding and the like. Further, by carrying out the bonding of the substrate layers 11, 12 and 13 under a pressure lower than atmospheric pressure, the respective areas of the introduction part 2, the channels 31 to 35, and the wells 41 to 45 into which the sample solution is introduced can be made to have a pressure lower than atmospheric pressure (e.g., 1/100 atmospheric pressure). When a material, such as PDMS, that in addition to being elastic is also impermeable to gases, is used for the substrate layer 11 that seals the wells 41 to 45, if these layers are left under a negative pressure (vacuum) after the substrate layers 11 and 12 have been bonded, the air that is present in the respective areas, such as the introduction part 2, passes through the substrate layer 11. Consequently, the interior of the microchip 1a can be made to have a pressure lower than atmospheric pressure (a vacuum). It is noted that the step of making the interior of the microchip 1a have a pressure lower than atmospheric pressure is not a necessary step in the method for fabricating the microchip according to an embodiment of the present technology.

In the microchip 1a for nucleic acid amplification reaction according to the present technology, reagents R1 and R2 that include a part of the substances required for the nucleic acid amplification reaction are contained in advance in the wells 41 to 45 that are analysis sites. Consequently, a nucleic acid amplification reaction can be started just by supplying the remaining substances required for the nucleic acid amplification reaction and the sample solution including the target nucleic acid amplification strand to the wells 41 to 45. Further, by containing the plurality of solid-phase reagents R1 and R2 in wells 41 to 45, the plurality of substances required for the nucleic acid amplification reaction can be held in the microchip 1a in a separated state until the start of analysis. Consequently, in a nucleic acid amplification reaction that uses the microchip 1a, the occurrence of primer dimers and the like due to primers annealing to each other can be suppressed, and non-specific amplification of the nucleic acid is reduced. In addition, by performing the preparation of the reagents R1 and R2 in individual containers, it is simple to solidify the substances that are used in the nucleic acid amplification reaction individually. Consequently, the method for fabricating the microchip for nucleic acid amplification reaction according to the present technology enables the fabrication of a microchip for nucleic acid amplification reaction that is capable of simple yet highly accurate analysis.

Figure 4:
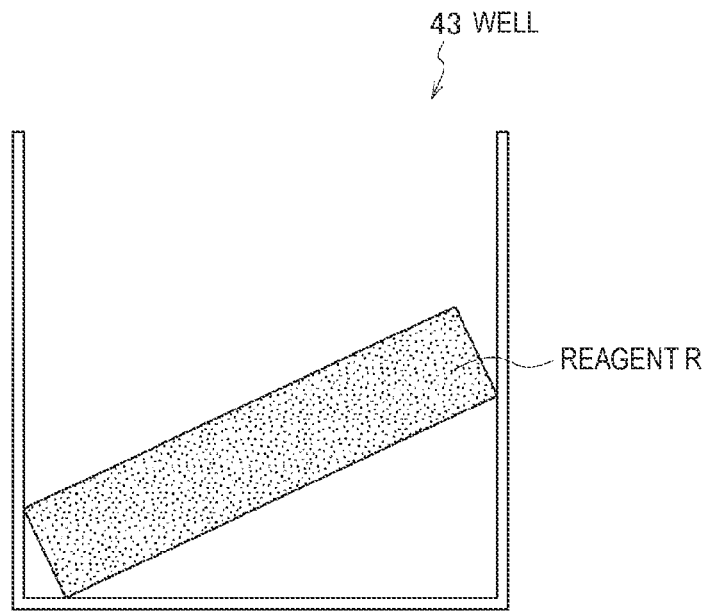

3. Configuration of the Microchip for Nucleic Acid Amplification Reaction According to a Modified Embodiment of the First Embodiment In FIG. 4, a well 43 is schematically illustrated as a representative for a reagent R that is contained in the wells of a microchip 1a-2 according to a modified embodiment of the first embodiment. Except for the composition of the reagent R contained in the respective wells, such as the wells 43, the microchip 1a-2 is the same as in the first embodiment. The parts that are the same as in the first embodiment are denoted with the same reference numerals, and a description thereof is omitted here. Further, the material of the substrate layers 11, 12, and 13 configuring the microchip 1a-2 is the same as the substrate layers denoted with the same reference numerals for the microchip 1a.

One type of reagent R is contained in the wells 43 of the microchip 1a-2. The fabrication steps of the microchip 1a-2 are the same as the flowchart illustrated in FIG. 3, except for the type of reagent solution that is prepared. Accordingly, a description of the fabrication steps will be omitted. As illustrated in well 43 of FIG. 4, the reagent R contained in the microchip 1a-2 may be a single type. For example, a reagent R including an enzyme may be contained in well 43, and the other components required for the nucleic acid amplification reaction, such as a primer, may be introduced into the microchip 1a-2 by mixing with the sample solution when the nucleic acid amplification reaction starts.

In the microchip 1a-2 according to the present technology, a part of the components required for a nucleic acid amplification reaction are contained in advance in the wells 41 to 45, so that the components included in the reagent R in the wells can be kept separate from the other components until the sample solution is introduced into the wells. Consequently, for example, an enzyme and a primer can be separated until the nucleic acid amplification reaction starts, so that non-specific nucleic acid amplification caused by primer dimers and the like is suppressed, which enables highly accurate analysis using the microchip 1a-2.

4. Configuration of the Microchip for Nucleic Acid Amplification Reaction According to a Second Embodiment of the Present Technology In FIG. 5, a well 43 is schematically illustrated as a representative for reagents R1 and R2 contained in the wells of a microchip 1b according to a second embodiment of the present technology. Except for the composition of the reagents R1 and R2 contained in the respective wells, such as the wells 43, the microchip 1b is the same as in the first embodiment. The parts that are the same as in the first embodiment are denoted with the same reference numerals, and a description thereof is omitted here. Further, the material of the substrate layers 11, 12, and 13 configuring the microchip 1b is the same as the substrate layers denoted with the same reference numerals for the microchip 1a.

Figure 5:
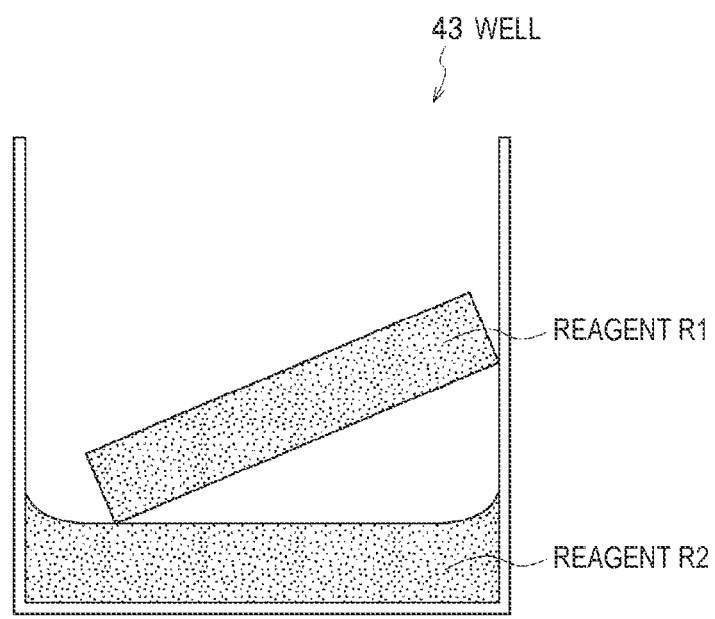
FIG. 5 is a schematic view illustrating a configuration in a well 43 of a microchip 1b according to a second embodiment of the present technology.

Similar to the reagents contained in the microchip 1a, the reagents R1 and R2 illustrated in FIG. 5 are solid-phase reagents that include at least a part of the substances required for a nucleic acid amplification reaction. Since the composition of the reagents R1 and R2 is the same as that of the reagents R1 and R2 contained in the microchip 1a, a description thereof is omitted. The difference between the reagents R1 and R2 contained in the microchip 1b and the reagents R1 and R2 contained in the microchip 1a is that a part of the reagents contained in the wells 43 is fixed in the well (refer to FIG. 5).

5. Method for Fabricating the Microchip for Nucleic Acid Amplification Reaction According to a First Embodiment of the Present Technology The method for fabricating the microchip 1b will now be described with reference to the flowchart illustrated in FIG. 6. Since the substrate layer molding step S1, the reagent solution preparation step S2, and the substrate layer bonding step S5, respectively, are the same as in the first embodiment, a description thereof will be omitted. The reagent solution fixing step S3b and the reagent containment step S4 will be described.

(1) Fixing of the Reagent Solutions

Figure 6:
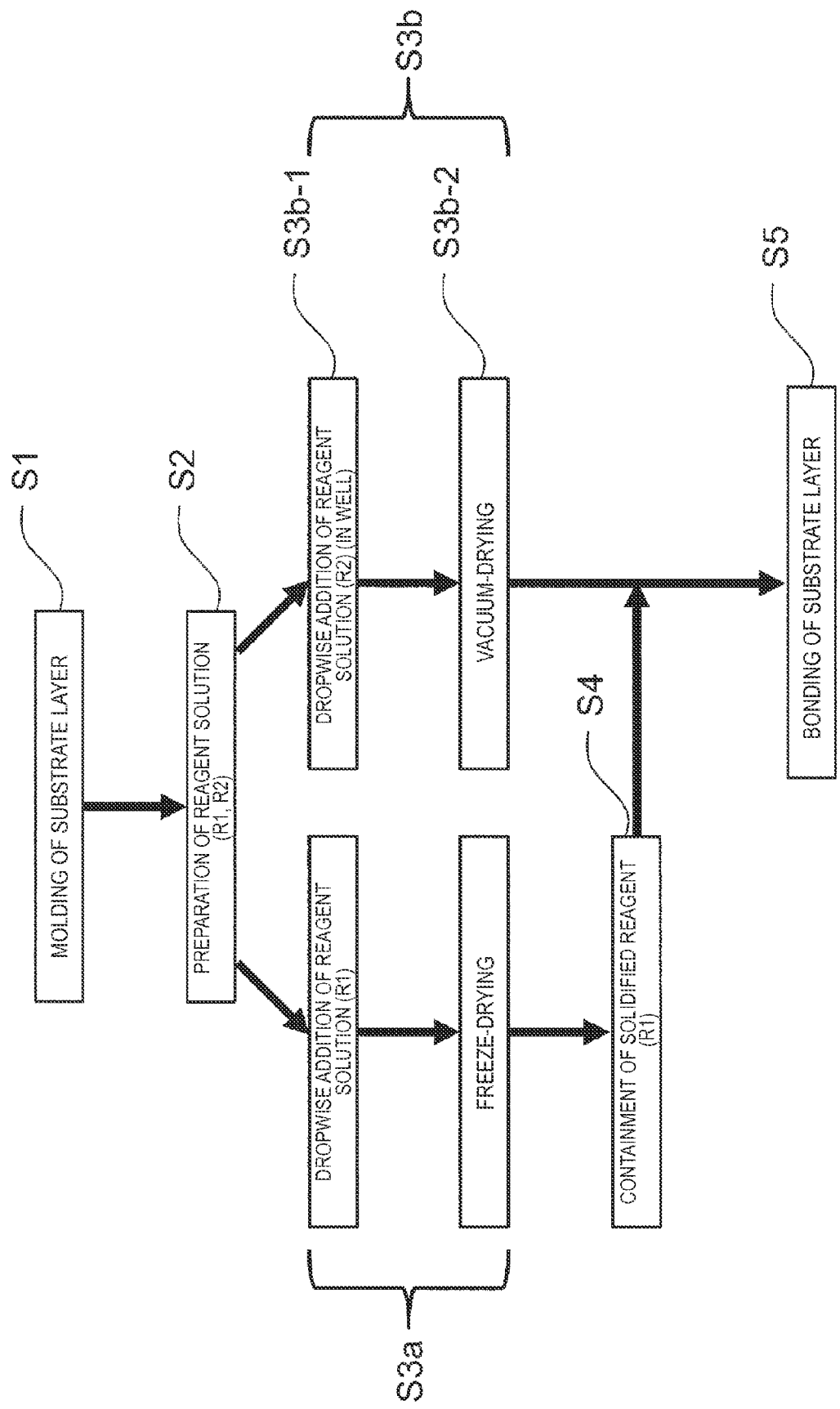
FIG. 6 is a flowchart illustrating a method for fabricating the microchip 1b.

In FIG. 6, reference symbol S3b represents a step of fixing the reagent solutions. In this step, among the plurality of types of reagent solution readied in the preparation step S2, one type of reagent solution is fixed in the wells 43. Namely, a reagent solution is dried in the wells 43, and the dried reagent solution is fixed in the well. The fixing step S3b will be described in order of a "reagent solution dropwise addition" step S3b-1 and a "vacuum-drying" step S3b-2 as illustrated in FIG. 6. Further, in the fabrication of the microchip 1b, the other reagent solution not used in the reagent solution fixing step S3b is turned into a solid state by the reagent solution solidification step S3a in the same manner as in the first embodiment.

Reagent Solution (R2) Dropwise Addition Step S3b-1

In this step, among the above-described reagent solutions prepared in the reagent solution preparation step S2, one type of reagent solution is added dropwise to each well formed in the substrate layer 12 and the like in molding step S1. At this stage, it is preferred that the substrate layer 12 in which the wells are formed has been cooled.

Vacuum-Drying Step S3b-2

In this step, the reagent solution is dried by placing the substrate layer 12 onto which the above-described reagent solution was added dropwise under a vacuum (600 to 1,000 Pa). Unlike the reagent solution solidification step S3a in the first embodiment, in this method it is necessary to select a drying method that does not change the shape of the substrate layer 12, so that vacuum-drying, for example, is preferred. The drying method may also be carried out by air drying, for example, according to the nature of the substances included in the reagent solution.

(2) Reagent Containment

In FIG. 6, reference symbol S4 represents a reagent containment step. As a result of the above-described reagent solution fixing step, unlike the first embodiment, the reagent R2 is present in the wells 43 in the microchip 1b. In this step, the reagent R1 readied in the reagent solution solidification step S3a is separately contained in the well in which this reagent R2 has been fixed. The solidified reagent solution R1 to be contained in the microchip 1b is not limited to being one type, it may be freely selected.

In the microchip 1b according to the present technology, reagents R1 and R2 that include a part of the substances required for a nucleic acid amplification reaction are held in advance in the wells 41 to 45 that are analysis sites. Consequently, similar to the microchip 1a, when performing a nucleic acid amplification reaction using the microchip 1b, the nucleic acid amplification reaction can be simply performed by introducing just the remaining substances required for the nucleic acid amplification reaction and the sample solution including the target nucleic acid amplification strand into the wells 41 to 45. Further, the components included in the plurality of solid-phase reagents R1 and R2 having different compositions that are held in the wells 41 to 45 and that have difference compositions can be maintained in separate states until the start of the nucleic acid amplification reaction. Consequently, by including, for example, an enzyme and a primer as the components included in the reagent R1 and reagent R2, respectively, non-specific amplification of the nucleic acid due to the occurrence of primer dimers can be suppressed.

6. Configuration of the Microchip for Nucleic Acid Amplification Reaction According to a Third Embodiment of the Present Technology In FIG. 7, a well 43 is schematically illustrated as a representative for a reagent R that is contained in the wells of a microchip 1c according to a third embodiment. Except for the composition of the reagent R contained in the respective wells, such as the wells 43, the microchip 1c is the same as in the first embodiment. The parts that are the same as in the first embodiment are denoted with the same reference numerals, and a description thereof is omitted here. Further, the material of the substrate layers 11, 12, and 13 configuring the microchip 1c is the same as the substrate layers denoted with the same reference numerals for the microchip 1a.

Figure 7:
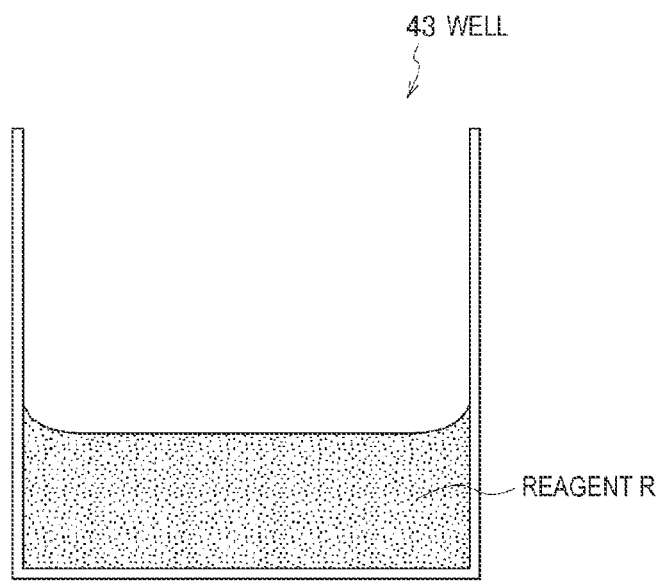
FIG. 7 is a schematic view illustrating a configuration in a well 43 of a microchip 1c according to a third embodiment of the present technology.

The reagent R, which includes at least a part of the substances required to obtain a nucleic acid amplification strand in a nucleic acid amplification reaction, is fixed in the wells 43 of the microchip 1c (FIG. 7). The components required for the nucleic acid amplification reaction that are included in the reagent R may be a single type, or a plurality of types.

In the fabrication steps of the microchip 1c, since the substrate layer molding step S1, the reagent solution preparation step S2, and the substrate layer bonding step S5 are the same as in the first embodiment, a description thereof will be omitted. Similar to the reagent solution fixing step S3b in the second embodiment, the step of fixing a reagent solution in the wells 43 is carried out by adding a reagent solution prepared to a predetermined composition dropwise to each well provided on the substrate layer 12, and fixing the reagent solution in the wells 43 by vacuum-drying or the like.

During the dropwise addition of the reagent solution, it is preferred that the prepared reagent solution is stored at a cool temperature. Further, it is preferred that the substrate layer 12 in which the respective wells are formed is also stored at a cool temperature. For example, the equipment holding the substrate layer 12, such as an aluminum block, may be cooled in advance in a freezer, and the dropwise addition of the reagent solution carried out by placing the substrate layer 12 on the cooled equipment. In the microchip 1c, the reagent R fixed in the wells 43 and the like may be a single type, or may be reagents R1 and R2 having different compositions. If a plurality of reagents R1 and R2 are fixed in the wells 43, the dropwise addition of the reagent solution may be carried out by adding either of the reagent solutions dropwise into the wells 43 and fixing by vacuum-drying or the like, then adding dropwise the next reagent solution onto the fixed reagent R1 and drying, and then repeating these steps.

By maintaining the reagent solutions at a low temperature from the reagent solution preparation step until the reagent solution drying step, bonding of the substances and enzyme activity are suppressed for the components that are required for the nucleic acid amplification reaction which are included in the reagent solution.

Consequently, the occurrence of primer dimers is suppressed, and non-specific amplification of the nucleic acid is reduced.

Aspects of the present technology may include the following.

(1) A method for fabricating a microchip for nucleic acid amplification reaction, including a solidification step of drying a reagent solution including at least a part of substances required for a nucleic acid amplification reaction, and a containment step of arranging the solidified reagent solution in wells that serve as a reaction site for a nucleic acid amplification reaction.

(2) The method for fabricating a microchip for nucleic acid amplification reaction according to (1), wherein the solidification step includes a step of freeze-drying the reagent solution.

(3) The method for fabricating a microchip for nucleic acid amplification reaction according to (1) or (2), further including a preparation step of readying a plurality of the reagent solutions that have different compositions, wherein the reagent solutions are a first reagent solution that includes an oligonucleotide primer but not an enzyme, and a second reagent solution that includes an enzyme but not an oligonucleotide primer.

(4) The method for fabricating a microchip for nucleic acid amplification reaction according to (3), wherein the solidification step includes a step of individually freeze-drying the first reagent solution and the second reagent solution.
(5) The method for fabricating a microchip for nucleic acid amplification reaction according to (3) or (4), wherein the containment step includes a step of containing the first reagent solution that has been solidified and that includes two or more kinds of oligonucleotide primer in each of a plurality of the wells.
(6) The method for fabricating a microchip for nucleic acid amplification reaction according to (3), further including, before solidifying either one of the first reagent solution and the second reagent solution in the solidification step and performing the containment step, a fixing step of adding the reagent solution not used in the solidification step dropwise into the wells and drying in the wells.
(7) The method for fabricating a microchip for nucleic acid amplification reaction according to (6), wherein the fixing step includes a step of vacuum-drying the reagent solution.

EXAMPLES

Example 1

1. Detection of Non-Specific Amplification in a Nucleic Acid Amplification Reaction The suppression of non-specific amplification of a nucleic acid strand in a nucleic acid amplification reaction in which the microchip according to the present technology is used was verified.
Materials and Methods
1. Microchip Fabrication
Four types of microchip whose methods and the like of producing the reagent to be contained were different were used as the microchips used in the present example. For all four types of microchip, substrates made from PDMS and glass were used as materials. Further, as the reagent required for the nucleic acid amplification reaction performed in the present example, four types of primer used for amplification of influenza type A, Bst DNA polymerase, dNTPs, and a reaction buffer solution were readied. The steps from the reagent solution preparation step until the containment step will be described below for each microchip.
<1> Microchip 1
As a comparative example of the microchip for nucleic acid amplification reaction according to the present technology, microchip 1 (hereinafter referred to as "M1") was fabricated. In the fabrication of M1, a reagent solution including four types of primer, Bst DNA polymerase, dNTPs, and a reaction buffer solution was prepared. 1.2 µL of the reagent solution was added dropwise into the wells formed in the substrate layer, and the reagent solution in the wells was fixed by a vacuum-drying treatment (about 1,000 Pa) of about 2 hours.
<2> Microchip 2
Microchip 2 (hereinafter referred to as "M2") is a microchip in which a solidified reagent is contained in the wells. In the fabrication of M2, the preparation of a reagent solution including four types of primer, Bst DNA polymerase, dNTPs, and a reaction buffer solution was carried out under cooling by placing the solidification container over ice. The reagent solution was frozen by leaving the solidification container containing 1.2 µL of reagent solution for 6 hours at −40° C. After the reagent solution had frozen, the solidification container was set in a freeze dryer (FDU-2200, EYELA). The reagent solution was dried for 12 hours or more in a vacuum (about 6 to 8 Pa) with the reagent solution kept in a frozen state. Then, the temperature of the drying chamber was set to 30° C., and the reagent solution was dried for a further 6 hours or more. The reagent solidified by the freeze-drying was removed from the solidification container, and placed in the wells formed in the substrate layer.
<3> Microchip 3
Microchip 3 (hereinafter referred to as "M3") is a microchip in which a plurality of solidified reagents containing different substances are contained in the wells. In the fabrication of M3, a reagent solution including, among the components required for the nucleic acid amplification reaction of four types of primer, Bst DNA polymerase, dNTPs, and a reaction buffer solution, the primers (hereinafter referred to as "FluA") was prepared while cooling. Further, a reagent solution including the Bst DNA polymerase, the dNTPs, and the reaction buffer solution (hereinafter referred to as "RM") was prepared while cooling. The prepared reagent solutions were added dropwise (0.4 µl for FluA and 0.8 µl for RM) into separate solidification containers. The respective reagent solutions in the solidification containers were solidified by freeze-drying in the same manner as for M2. The solidified FluA and RM were removed from the solidification containers, and placed in each of the wells formed in the substrate layer so that both FluA and RM were contained in each well.
<4> Microchip 4
Microchip 4 (hereinafter referred to as "M4") is a microchip in which reagents containing different components were fixed in the wells over a plurality of times. In the fabrication of M4, the reagent solution FluA and the reagent solution RM were prepared in the same manner as M2. 0.4 µl of FluA was added dropwise into the wells, and fixed in the wells by vacuum-drying in the same manner as for M1. The substrate layer having the wells in which the FluA had been fixed was cooled and maintained at a low temperature, and in that state 0.8 µl of RM was added dropwise into the wells in which the FluA was fixed. Vacuum-drying was carried out again in the same manner as for M1 to fix the RM in the wells.

Figure 8:
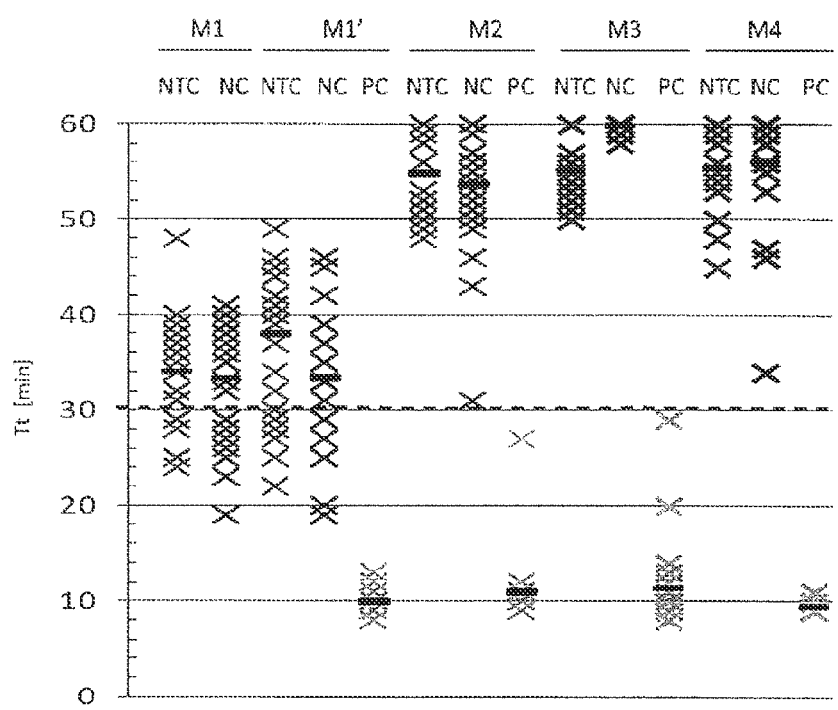
FIG. 8 is a graph illustrating a start time of nucleic acid amplification in a microchip according to the present technology.

The substrate layer having the wells in which the reagent was contained or had been fixed of the above four types of microchip was laminated with another substrate layer to seal the wells. The surface of each substrate layer was treated by oxygen plasma irradiation ($O_2$: 10 cc, RF output: 100 W, RF irradiation time: 30 seconds) and bonded under a vacuum to complete the microchips M1 to M4.
2. Nucleic Acid Amplification Reaction
A nucleic acid amplification reaction was carried out using the microchips M1 to M4 fabricated by the above-described steps. A LAMP method was employed for the nucleic acid amplification. A sample solution was charged into M1 to M4, and the nucleic acid amplification reaction was carried out at 63° C. For the sample solutions, an influenza type A positive specimen (positive control, hereinafter referred to as "PC"), an influenza type A negative specimen (negative control, hereinafter referred to as "NC"), and water (non-template control, hereinafter referred to as "NTC") were used. Detection of the nucleic acid strands was carried out by fluorescence detection, and SYBR Green was used for the detection reagent.
Results
The results of the present example are shown in FIG. 8. FIG. 8 shows the start of nucleic acid amplification in each of the microchips M1 to M4 for each sample solution. The nucleic acid amplification start time is defined as the time at which an amplification curve plotting the fluorescence intensity obtained by SYBR Green rises up and reaches a predetermined threshold. It is noted that the Mr in FIG. 8 is a microchip fabricated by the same fabrication steps as for M1, and which was used in a nucleic acid amplification reaction in the same manner as M1.

Based on the results of the nucleic acid amplification reaction, nucleic acid amplification was detected in the wells that the PC was introduced into for the microchips M1 to M4 (regarding M1, refer to M1'). Namely, it was shown that the reagent contained in the wells was stored in a state that could be used in a nucleic acid amplification reaction. On the other hand, nucleic acid amplification was observed also for the microchips M1 to M4 into which the NC and the NTC had been introduced. This indicates that non-specific amplification of the nucleic acid strand occurred in the wells of the microchips M1 to M4. In the nucleic acid amplification reaction performed in the present example, specific amplification for a template nucleic acid strand of a nucleic acid was detected within 30 minutes of the start of the nucleic acid amplification reaction (FIG. 8). Consequently, the fact that nucleic acid amplification occurred within 30 minutes of the reaction starting in the wells into which NC and NTC had been introduced, in which nucleic acid amplification should not occur, impairs analysis using the microchips.

As illustrated in FIG. 8, the start of non-specific nucleic acid amplification in M3 was more than 50 minutes after the start of the nucleic acid amplification reaction. On the other hand, the start of non-specific nucleic acid amplification in the comparative example M1 was detected about 20 minutes after the start of the reaction. From this result, it was shown that non-specific nucleic acid amplification is suppressed in the nucleic acid amplification reaction using M3.

The start of non-specific nucleic acid amplification in M2 and M4 was, in some of the wells, after about 30 minutes had passed. Compared with the M3 results, in the results for M2 and M4 the start time of non-specific nucleic acid amplification was earlier. However, nucleic acid amplification was not deemed to have occurred for NTC and NC within 30 minutes of the start of the nucleic acid amplification reaction. From this result, it was shown that in M2 and M4, non-specific nucleic acid amplification was suppressed more than in M1 (comparative example). Further, the suppression effect of non-specific nucleic acid amplification was about the same in M2 and M4.

From the results of the present example, the suppression of non-specific nucleic acid amplification in a nucleic acid amplification reaction by using a microchip that contained a reagent including the substances required for the nucleic acid amplification reaction in the wells was confirmed. Especially, non-specific nucleic acid amplification was greatly suppressed for the microchip (M3) in which a reagent solution that included a primer but did not include an enzyme and reagent solution that included an enzyme but did not include a primer were individually solidified and sealed in wells. Namely, with a microchip fabricated based on the microchip fabrication method according to the present technology, non-specific nucleic acid amplification is reduced and analysis accuracy is improved.

Further, even in the microchip (M2) that contained a solid-phase reagent including an enzyme and a primer, and the microchip (M4) fabricated by adding a reagent solution including an enzyme dropwise into wells in which a reagent including a primer had been fixed, the suppression of non-specific nucleic acid amplification was observed. This indicates that non-specific nucleic acid amplification is suppressed in a nucleic acid amplification reaction that uses a reagent that was dried after the mixing of a cooled enzyme and a primer in the microchip fabrication steps. Based on the above, it was confirmed that the microchip nucleic acid amplification reaction according to the present technology not only enables analysis to be carried out simply just by the introduction of a sample solution and the like, but since non-specific nucleic acid amplification is suppressed, also enables highly accurate analysis.

INDUSTRIAL APPLICABILITY

According to the microchip for nucleic acid amplification reaction according to the present technology, analysis based on nucleic acid amplification can be carried out simply and accurately. Consequently, the microchip for nucleic acid amplification reaction according to the present technology can be used as a device that performs nucleic acid amplification for clinical genotyping and contagion determination.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

R, R1, R2 reagent
1a, 1a-2, 1b, 1c microchip
11, 12, 13 substrate layer
2 introduction part
31, 32, 33, 34, 35 channel
41, 42, 43, 44, 45 wells

The invention claimed is:

1. A method for fabricating a microchip for nucleic acid amplification reaction, the method comprising:
   a solidification step of drying a reagent solution including at least a part of substances required for a nucleic acid amplification reaction, the reagent solution including a first reagent solution and a second reagent solution; and
   a containment step occurring after the solidification step, the containment step including arranging the solidified reagent solution in a well that serves as a reaction site for a nucleic acid amplification reaction such that the solidified first reagent solution is separated from the solidified second reagent solution in the well.

2. The method for fabricating a microchip for nucleic acid amplification reaction according to claim 1, wherein the solidification step includes a step of freeze-drying at least one of the first reagent solution and the second reagent solution.

3. The method for fabricating a microchip for nucleic acid amplification reaction according to claim 2, the method comprising:
   a preparation step of readying, prior to the solidification step, the first and second reagent solutions that have different compositions,
   wherein the first reagent solution includes an oligonucleotide primer but not an enzyme, and the second reagent solution includes an enzyme but not an oligonucleotide primer.

4. The method for fabricating a microchip for nucleic acid amplification reaction according to claim 3, wherein the solidification step includes a step of individually and separately freeze-drying the first reagent solution and the second reagent solution.

5. The method for fabricating a microchip for nucleic acid amplification reaction according to claim 4, wherein the containment step includes a step of containing the first reagent solution that has been solidified and that includes two or more kinds of oligonucleotide primer in each of a plurality of the wells.

6. The method for fabricating a microchip for nucleic acid amplification reaction according to claim 3, the method comprising:
 solidifying either one of the first reagent solution and the second reagent solution in the solidification step, and, prior to the containment step, a fixing step of adding the reagent solution not used in the solidification step dropwise into the wells and drying in the wells.

7. The method for fabricating a microchip for nucleic acid amplification reaction according to claim 6, wherein the fixing step includes a step of vacuum-drying the reagent solution.

* * * * *